US007799962B2

(12) United States Patent
Dakka et al.

(10) Patent No.: US 7,799,962 B2
(45) Date of Patent: *Sep. 21, 2010

(54) PROCESS FOR AROMATIC ALKYLATION

(75) Inventors: Jihad Mohammed Dakka, Whitehouse Station, NJ (US); John Scott Buchanan, Lambertville, NJ (US); Robert Andrew Crane, Hellertown, PA (US); Christine Nicole Elia, Bridgewater, NJ (US); Xiaobing Feng, Houston, TX (US); Larry Lee Iaccino, Seabrook, TX (US); Gary David Mohr, Houston, TX (US); Brenda Anne Raich, Annandale, NJ (US); Jose' Guadalupe Santiesteban, Baton Rouge, LA (US); Lei Zhang, Bridgewater, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 24 days.

This patent is subject to a terminal disclaimer.

(21) Appl. No.: 12/208,011

(22) Filed: Sep. 10, 2008

(65) Prior Publication Data
US 2009/0012338 A1    Jan. 8, 2009

Related U.S. Application Data

(63) Continuation of application No. 10/987,324, filed on Nov. 12, 2004, now Pat. No. 7,453,018.

(60) Provisional application No. 60/533,951, filed on Dec. 31, 2003.

(51) Int. Cl.
*C07C 2/68* (2006.01)

(52) U.S. Cl. ...................... 585/467; 585/906
(58) Field of Classification Search ............... 585/467, 585/906
See application file for complete search history.

(56) References Cited

U.S. PATENT DOCUMENTS

| 3,354,078 A | 11/1967 | Miale et al. |
| 3,965,207 A | 6/1976 | Weinstein |
| 4,086,287 A | 4/1978 | Kaeding et al. |
| 4,409,132 A * | 10/1983 | Forbus et al. ............. 502/62 |
| 4,504,690 A | 3/1985 | Forbus et al. |
| RE31,919 E | 6/1985 | Butter et al. |
| 4,548,914 A | 10/1985 | Chu |
| 4,670,616 A | 6/1987 | De Simone et al. |
| 4,899,007 A | 2/1990 | Chu et al. |
| 5,530,170 A | 6/1996 | Beck et al. |
| 5,633,417 A | 5/1997 | Beck et al. |
| 5,665,325 A | 9/1997 | Verduijn |
| 5,675,047 A | 10/1997 | Beck et al. |
| 5,698,756 A | 12/1997 | Beck et al. |
| 5,993,642 A | 11/1999 | Mohr et al. |
| 5,994,603 A | 11/1999 | Mohr et al. |
| 6,576,582 B1 | 6/2003 | Beck et al. |

FOREIGN PATENT DOCUMENTS

| EP | 296582 | 12/1988 |
| GB | 1 574 523 | 9/1980 |
| JP | S56-045419 | 4/1981 |
| JP | S58-035127 | 3/1983 |
| JP | S60-067437 | 4/1985 |
| JP | H1-199920 | 8/1989 |
| JP | 01/524069 | 11/2001 |
| JP | 03/513058 | 4/2003 |
| WO | 98/14415 | 4/1998 |
| WO | 01/32591 | 5/2001 |

OTHER PUBLICATIONS

Pool et al., "An Electron Spin Resonance Study of Coke Deposits on a Silica-Alumina Catalyst", Journal of Catalysis, 4, (1965), pp. 518-522.
Olson et al., "Chemical and Physical Properties of the ZSM-5 Substitutional Series", Journal of Catalysis, 61, (1980), pp. 390-396.
Miale et al., "Catalysis by Crystalline Aluminosilicates", Journal of Catalysis, 6, (1966), pp. 278-287.
Baerlocher et al., "Atlas of Zeolite Framework Types", 2001, Fifth Edition.

* cited by examiner

*Primary Examiner*—Thuan Dinh Dang
(74) *Attorney, Agent, or Firm*—Andrew B. Griffis

(57) ABSTRACT

This invention relates to a process for the selective alkylation of toluene and/or benzene with an oxygen-containing alkylation agent. In particular, the process uses a selectivated molecular sieve which has been modified by the addition of a hydrogenation component, wherein at least one of the following conditions is met: (a) the selectivated molecular sieve has an alpha value of less than 100 prior to the addition of the hydrogenation component, or (b) the selectivated and hydrogenated catalyst has an alpha value of less than 100. The process of this invention provides high selectivity for the alkylated product while reducing catalyst degradation.

16 Claims, 11 Drawing Sheets

Toluene Methylation over Catalyst A

Toluene Methylation over Catalyst B

Toluene Conversion over Catalysts C, D, and E

P-Xylene Selectivity over Catalysts C, D, and E

Methanol Utilization over Catalysts C, D, and E

Toluene Methylation over Catalyst F

Toluene Methylation over Catalyst K
Tol:MeOH 3:1, H2/HC 1:1, H2HC 1:1, S.V. 8, Press 50 PSIG, Temp 500°C Toluene Methylation over Catalyst L
Tol:MeOH 3, H2/HC 2, H2HC 1, S.V. 8, Press 50 PSIG, Temp 500°C Effect of hydrogenation metals/water and phosphorus on methanol decomposition Toluene Methylation over Catalyst M
Tol:MeOH 3, H2:HC 2, H2O:HC 1, S.V. 8, Press 50 PSIG, Temp 500°C Toluene Methylation over Catalyst N Toluene Methylation over Catalyst O Toluene Methylation over Catalyst P Toluene Methylation over Catalyst Q

PROCESS FOR AROMATIC ALKYLATION

CROSS REFERENCE TO RELATED APPLICATIONS

This application is a continuation of U.S. application Ser. No. 10/987,324, filed Nov. 12, 2004, now U.S. Pat. No. 7,453,018, which claims the benefit of U.S. Provisional Application No. 60/533,951, filed Dec. 31, 2003, both hereby incorporated herein by reference.

FIELD OF THE INVENTION

The present invention relates to a process for the selective alkylation of toluene, benzene, naphthalene, alkyl naphthalene and mixtures thereof with an oxygen-containing alkylation agent. In particular, the process uses a catalyst comprising a selectivated molecular sieve which has been modified by the addition of at least one hydrogenation component, wherein at least one of the following conditions is met: (a) the selectivated molecular sieve has an alpha value of less than 100 prior to the incorporation the hydrogenation component, or (b) the selectivated and hydrogenated molecular sieve used in the selective alkylation process has an alpha value of less than 100. The process of this invention provides high selectivity for the alkylated product while reducing catalyst deactivation.

BACKGROUND OF THE INVENTION

Of the xylene isomers, i.e. ortho-, meta-, and para-xylenes, the para-xylene isomer is of particular value as a large volume chemical intermediate. One method for manufacturing para-xylene is by disproportionation of toluene into xylenes. However, a disadvantage of this process is that large quantities of benzene are also produced. Another process for manufacturing para-xylene is the isomerization of a feedstream that contains non-equilibrium quantities of mixed ortho- and meta-xylene isomers and is lean with respect to para-xylene content. A disadvantage of this process is that the separation of the para-xylene from the other isomers is expensive.

There is growing interest in the alkylation of toluene with methanol as a next generation method for producing para-xylene. This technology can theoretically produce twice the yield of para-xylene from toluene, compared to the toluene disproportionation process. Examples of such toluene methylation processes include U.S. Pat. No. 3,965,207, which involves the methylation of toluene with methanol using a molecular sieve catalyst such as ZSM-5. U.S. Pat. No. 4,670,616 involves the production of xylenes by the methylation of toluene with methanol using a borosilicate zeolite catalyst which is bound by a binder such as alumina, silica, or alumina-silica.

A disadvantage of known toluene methylation catalysts is that methanol selectivity to para-xylene, the desirable product, has been low, in the range of 50-60%. The balance is wasted on the production of coke and other undesirable products. Attempts to increase the para-xylene selectivity have been conducted, however, it has been found that as para-xylene selectivity increases, the lifespan of the catalyst decreases. It is believed that the rapid catalyst deactivation is due to build up of coke and heavy by-products on the catalyst. The limited catalyst lifespan typically necessitates the use of a fluidized bed reactor wherein the catalyst is continuously regenerated. However, such a system usually requires high capital investment. A preferred system for toluene methylation is to use a fixed bed reactor because of lower capital investment. However, until a suitable catalyst is found that provides a sufficient lifespan, with a sufficient selectivity to the desired product, fixed bed systems are simply impractical. There remains a need for an improved toluene methylation process having a catalytic system that minimizes or avoids the disadvantages of prior systems, which includes low para-xylene selectivity and rapid catalyst deactivation. The present invention satisfies this need.

SUMMARY OF THE INVENTION

The invention is a process for forming a selectively alkylated aromatic compound comprising reacting an alkylating agent with a feed comprising an aromatic compound selected from the group consisting of toluene, benzene, naphthalene, alkyl naphthalene and mixtures thereof in the presence of a catalyst under alkylation reaction conditions, said catalyst comprising a selectivated molecular sieve and at least one hydrogenation metal, wherein at least one of the following conditions is satisfied: (a) the selectivated molecular sieve has an alpha value of less than 100 prior to incorporation of said at least one hydrogenation metal, or (b) the selectivated and hydrogenated molecular sieve has an alpha value of less than 100.

DETAILED DESCRIPTION OF THE INVENTION

Figure 1:
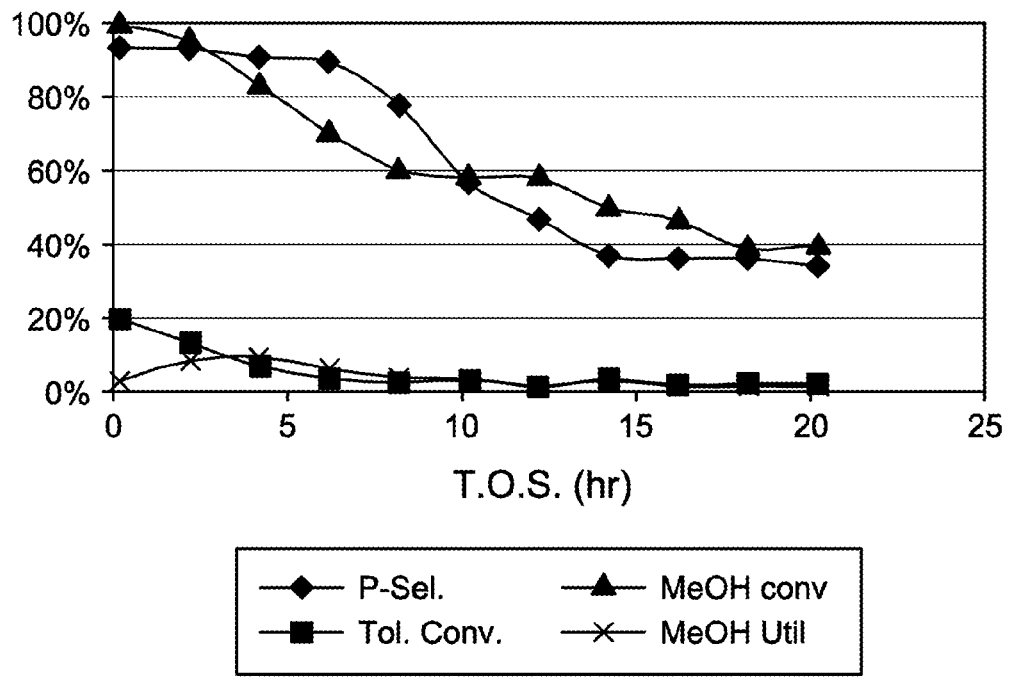
FIGS. 1-12 and 14-18 are plots showing the para-selectivity of various catalysts in a toluene methylation process.

The present invention relates to a process for the selective alkylation of toluene, benzene, naphthalene, alkyl naphthalene and mixtures thereof with an oxygen-containing alkylation agent. The process uses a catalyst comprising a selectivated molecular sieve, preferably a para-selective molecular sieve, that has been modified by the addition of at least one hydrogenation component. In accordance with this invention, at least one of the following conditions should also be met: (a) the selectivated molecular sieve has an alpha value of less than 100 prior to the incorporation of the hydrogenation component, or (b) the selectivated and hydrogenated molecular sieve has an alpha value of less than 100. The catalyst, when used in this process, has an extended catalyst lifetime, while providing para-selectivity of greater than 60%, more preferably greater than 75%, more preferably greater than 80%, even more preferably greater than 85% and most preferably greater than 90%. Preferably, the process is a toluene or benzene methylation process, which forms para-xylene at these preferred para-selectivity ranges.

Catalysts suitable for use in the present invention include any catalyst that is effective for the alkylation of toluene, benzene, naphthalene, alkyl naphthalene or mixtures thereof. Preferably, the catalyst will be effective for the preferred process of toluene or benzene methylation. Catalysts used in the present invention include naturally occurring and synthetic crystalline molecular sieves. Examples of such molecular sieves include large pore molecular sieves, intermediate size pore molecular sieves, and small pore molecular sieves. These molecular sieves are described in "Atlas of Zeolite Framework Types", eds. Ch. Baerlocher, W. H. Meier, and D. H. Olson, Elsevier, Fifth Edition, 2001, which is hereby incorporated by reference. A large pore molecular sieve generally has a pore size of at least about 7 Å and includes IWW, LTL, VFI, MAZ, MEI, FAU, EMT, OFF, *BEA, and MOR structure type molecular sieves (IUPAC Commission of Zeolite Nomenclature). Examples of large pore molecular sieves, include ITQ-22, mazzite, offretite, zeolite L, VPI-5, zeolite Y, zeolite X, omega, Beta, ZSM-3, ZSM-4, ZSM-18, ZSM-20, SAPO-37, and MCM-22. An intermediate pore size molecular sieve generally has a pore size from about 5 Å to about 7 Å and includes, for example, ITH, ITW, MFI, MEL, MTW, EUO, MTT, HEU, FER, MFS, and TON structure type molecular sieves (IUPAC Commission of Zeolite Nomenclature). Examples of intermediate pore size molecular sieves, include ITQ-12, ITQ-13, ZSM-5, ZSM-12, ZSM-22, ZSM-23, ZSM-34, ZSM-35, ZSM-38, ZSM-48, ZSM-50, ZSM-57, silicalite, and silicalite 2. A small pore size molecular sieve has a pore size from about 3 Å to about 5 Å and includes, for example, CHA, ERI, KFI, LEV, and LTA structure type molecular sieves (IUPAC Commission of Zeolite Nomenclature). Examples of small pore molecular sieves include ZK-4, SAPO-34, SAPO-35, ZK-14, SAPO-42, ZK-21, ZK-22, ZK-5, ZK-20, zeolite A, erionite, chabazite, zeolite T, gmelinite, and clinoptilolite.

The intermediate pore size molecular sieve will generally be a composition having the following molar relationship:

$$X_2O_3:(n)YO_2$$

wherein X is a trivalent element such as aluminum, iron, boron, and/or gallium and Y is a tetravalent element such as silicon, tin, and/or germanium; and n has a value greater than 12, said value being dependent upon the particular type of molecular sieve and the desired alpha value of the molecular sieve, in accordance with this invention. When the intermediate pore size molecular sieve is a MFI structure type molecular sieve, n is preferably greater than 10 and preferably, from 20:1 to 200:1.

In accordance with this invention, the molecular sieve catalyst is selectivated for the production of the desired alkylated product, which in the preferred embodiment is para-xylene. The catalyst can be selectivated by treating its surface with compounds of phosphorus and/or magnesium and/or various metal oxides such as alkaline earth metal oxides, e.g., calcium oxide, magnesium oxide, etc. rare earth metal oxides, lanthanum oxide, and other metal oxides such as boron oxide, titania, antimony oxide, and manganese oxide. Preferred ranges for such treatment are from about 0.1 wt. % to 25 wt. %, more preferably from about 1 wt. % to about 10 wt. % of such compounds based on the weight of the catalyst. The selectivation may also be accomplished by depositing coke on the catalyst. Coke selectivation can be carried out during the methylation reaction, such as by running the methylation reaction at conditions which allow the deposition of coke on the catalyst. Also, the catalyst can be preselectivated with coke, for example, by exposing the catalyst in the reactor to a thermally decomposable organic compound, e.g., benzene, toluene, etc. at a temperature in excess of the decomposition temperature of said compound, e.g., from about 400° C. to about 650° C., more preferably 425° C. to about 550° C., at a WHSV in the range of from about 0.1 to about 20 lbs. of feed per pound of catalyst per hour, at a pressure in the range of from about 1 to about 100 atmospheres, and in the presence of 0 to about 2 moles of hydrogen, more preferably from about 0.1 to about 1 moles of hydrogen per mole of organic compound, and optionally in the presence of 0 to about 10 moles of nitrogen or another inert gas per mole of organic compound. This process is conducted for a period of time until a sufficient quantity of coke has deposited on the catalyst surface, generally at least about 2% by weight and more preferably from about 8% to about 40% by weight of coke.

A silicon compound may also be used to selectivate the catalyst. The silicon compound may comprise a polysiloxane including silicones, a siloxane, and a silane including disilanes and alkoxysilanes. As is known to those of ordinary skill in the art, multiple treatments may be employed to effect various degrees of selectivation.

Silicones that can be used to selectivate the catalyst include the following:

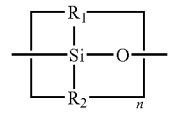

wherein $R_1$ is hydrogen, fluoride, hydroxy, alkyl, aralkyl, alkaryl or fluoro-alkyl. The hydrocarbon substituents generally contain from 1 to about 10 carbon atoms and preferably are methyl or ethyl groups. $R_2$ is selected from the same group as $R_1$, and n is an integer of at least 2 and generally in the range of 2 to about 1000. The molecular weight of the silicone employed is generally between about 80 to about 20,000 and preferably about 150 to about 10,000. Representative silicones include dimethylsilicone, diethylsilicone, phenylmethylsilicone, methyl hydrogensilicone, ethylhydrogensilicone, phenylhydrogensilicone, fluoropropylsilicone, ethyltrifluoroprophysilicone, tetrachlorophenyl methyl methylethylsilicone, phenylethylsilicone, diphenylsilicone, methyltrisilicone, tetrachlorophenylethyl silicone, methylvinylsilicone and ethylvinylsilicone. The silicone need not be linear but may be cyclic as for example hexamethylcyclotrisiloxane, octamethylcyclotetrasiloxane, hexaphenyl cyclotrisiloxane and octaphenylcyclotetrasiloxane. Mixtures of these compounds may also be used as well as silicones with other functional groups.

Useful siloxanes and polysiloxanes include as non-limiting example hexamethylcyclotrisiloxane, octamethylcyclotetrasiloxane, decamethyl cyclopentasiloxane, hexamethyldisiloxane, octamethylrisiloxane, decamethyltetrasiloxane, hexaethylcyclotrisiloxane, octaethylcyclo tetrasiloxane, hexaphenylcyclotrisiloxane and octaphenylcyclo-tetrasiloxane.

Useful silanes, disilanes, or alkoxysilanes include organic substituted silanes having the general formula:

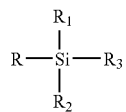

wherein R is a reactive group such as hydrogen, alkoxy, halogen, carboxy, amino, acetamide, trialkylsilyoxy, $R_1$, $R_2$ and $R_3$ can be the same as R or can be an organic radical which may include alkyl of from 1 to about 40 carbon atoms, alkyl or aryl carboxylic acid wherein the organic portion of alkyl contains 1 to about 30 carbon atoms and the aryl group contains about 6 to about 24 carbons which may be further substituted, alkylaryl and arylalkyl groups containing about 7 to about 30 carbon atoms. Preferably, the alkyl group for an alkyl silane is between about 1 and about 4 carbon atoms in chain length. Mixtures may also be used.

The silanes or disilanes include, as non-limiting examples, dimethylphenylsilane, phenylrimethylsilane, triethylsilane and hexamethyldislane. Useful alkoxysilanes are those with at least one silicon-hydrogen bond.

In a preferred embodiment, the molecular sieve catalyst is selectivated using the combined selectivation techniques of contacting the molecular sieve with a silicon compound and treatment with magnesium and/or phosphorus.

Usually the molecular sieve will be incorporated with binder material resistant to the temperature and other conditions employed in the process. Examples of suitable binder material include clays, alumina, silica, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The molecular sieve may also be composited with zeolitic material such as the zeolitic materials that are disclosed in U.S. Pat. No. 5,993,642.

The relative proportions of molecular sieve and binder material will vary widely with the molecular sieve content ranging from between about 1 to about 99 percent by weight, more preferably in the range of about 10 to about 70 percent by weight of molecular sieve, and still more preferably from about 20 to about 50 percent.

Catalysts particularly suited for the methylation reaction are zeolite bound zeolite catalysts. These catalysts, as well as their method of preparation, are described in U.S. Pat. No. 5,994,603, which is hereby incorporated by reference. The zeolite bound zeolite catalysts will comprise first crystals of an acidic intermediate pore size first molecular sieve and a binder comprising second crystals of a second molecular sieve. Preferably, the zeolite bound zeolite catalyst contains less than 10 percent by weight based on the total weight of the first and second zeolite of non-zeolitic binder, e.g., amorphous binder. An example of such a catalyst comprises first crystals of a MFI or MEL structure type, e.g., ZSM-5 or ZSM-11, and a binder comprising second crystals of MFI or MEL structure type, e.g., Silicalite 1 or Silicalite 2.

Hydrogenation metals useful in accordance with this invention encompass such metal or metals in the elemental state (i.e. zero valent) or in some other catalytically active form such as an oxide, sulfide, halide, carboxylate and the like. Preferably, the metal is used in its elemental state. Examples of suitable hydrogenation metals include Group VIIIA metals (i.e., Pt, Pd, Ir, Rh, Os, Ru, Ni, Co and Fe), Group IVB metals (i.e., Sn and Pb), Group VB metals (i.e., Sb and Bi), and Group VIIA metals (i.e., Mn, Tc and Re). Noble metals (i.e., Pt, Pd, Ir, Rh, Os and Ru) are sometimes preferred, most preferably Rh. The hydrogenation component may also be accompanied by another metal promoter.

The amount of Group VIIIA hydrogenation metal present on the catalyst will usually be from about 0.1 wt. % to about 5 wt. % of hydrogenation metal based on the weight of the catalyst. The incorporation of the hydrogenation metal can be accomplished with various techniques known to those skilled in the art. For example, the metal can be incorporated into the catalyst by impregnation, or by ion exchange of an aqueous solution containing the appropriate salt, or by a combination of these methods. By way of example, in an ion exchange process, platinum can be introduced by using cationic platinum complexes such as tetraammine-platinum (II) nitrate. In addition, the hydrogenation function can be present by physical intimate admixing, that is, the hydrogenation function can be physically mixed or extruded with the active catalyst. Physical intimate admixing can also be conducted by incorporating the hydrogenation function on a particle separate from the active catalyst, and then the particle carrying the hydrogenation function placed in close proximity to the catalyst. For example, the hydrogenation metal can be impregnated onto an amorphous support that is co-mingled with the active molecular sieve catalyst such as described in U.S. Pat. No. Re. 31,919 to Butter et al., incorporated by reference herein.

Typical alkylating agents include methanol, dimethylether, methylchloride, methylbromide, methylcarbonate, acetaldehyde, dimethoxyethane, acetone, and dimethylsulfide. For a toluene or benzene methylation process, the preferred methylating agents are methanol and dimethylether. The methylating agent can also be formed from synthesis gas, e.g., the agent can be formed from the H2, CO, and/or CO2 of synthesis gas. The methylating agent can be formed from the synthesis gas within the methylation reaction zone. One skilled in the art will know that other methylating agents may be employed to methylate the benzene and/or toluene based on the description provided therein.

In accordance with this invention, either (a) the selectivated molecular sieve or (b) the selectivated and hydrogenated molecular sieve used in the alkylating process will have an alpha value of less than 100, more preferably less than 50, even more preferably less than 25, and most preferably less than 10. As used herein, the alpha value is a measurement of the Bronsted acid activity of the selectivated molecular sieve, i.e. it discounts the effects of the addition of the hydrogenation component on the alpha value of the molecular sieve. The alpha test is described in U.S. Pat. No. 3,354,078 and in the Journal of Catalysis, Vol. 4, 522-529 (1965); Vol. 6, 278 (1966); and Vol. 61, 395 (1980), each incorporated herein by referenced. The experimental conditions of the alpha test preferably include a constant temperature of 538° C. and a variable flow rate as described in detail in the Journal of Catalysis, Vol. 61, 395 (1980). Typically, molecular sieves having a higher silica to alumina ratio will have a lower alpha value. Regardless, the alpha activity of a catalyst can be reduced in accordance with techniques known to those of ordinary skill in the art. For example, the alpha activity of a catalyst may be reduced by (1) steaming the catalyst at appropriate conditions, or (2) ion exchanging the catalyst with cations such as alkali metal ions.

The alkylation reaction can be carried out in vapor phase. Reaction conditions suitable for use in the present invention include temperatures from about 300° C. to about 700° C. and preferably about 400° C. to about 700° C. The reaction is preferably carried out at a pressure from about 1 to 1000 psig, more preferably from about 1 to 150 psig, and even more preferably about 1 to 50 psig. The reaction is preferably carried out at a weight hourly space velocity of between about 0.1 and about 200, more preferably between about 1 to about 20, and even more preferably between about 6 and 12, and preferably between about 1 and about 100 weight of charge per weight of catalyst per hour. The molar ratio of toluene and benzene to alkylating agent can vary and will usually be from about 0.1:1 to about 20:1. Preferred ratios for operation are in the range of 2:1 to about 4:1. The alkylating agent is usually supplied to the reaction zone through multiple feed points, e.g., 3-6 feed points. The process is preferably conducted in the presence of hydrogen at a partial pressure of at least 5 psi. Preferably, the system also includes water added to the feed, such that the molar ratio of hydrogen and/or added water to the aromatic compound and alkylating agent in the feed is between about 0.01 to about 10.

In an embodiment, the molecular sieve used in accordance with this invention has a hydrogenation metal comprising rhodium. The use of rhodium as the hydrogenation component has been found to reduce the amount of synthesis gas formed due to the decomposition of the alkylating agent (i.e. methanol in the preferred embodiment).

In another embodiment, the molecular sieve used in accordance with this invention has a hydrogenation metal comprising platinum, and a selectivating compound comprising phosphorus. When such a molecular sieve is used in the process of this invention, and wherein water is co-fed into the reactor, the amount of synthesis gas formed due to the decomposition of the alkylating agent (i.e. methanol in the preferred embodiment) is found to be reduced.

EXAMPLES

Example 1

4× Silica-Selectivated, 0.1% Pt Impregnated H-ZSM-5/SiO$_2$ (Catalyst A)

Silica-bound H-ZSM-5 (0.4 μm, 26:1 Si:Al$_2$) extrudate (65/35 ZSM-5/SiO$_2$, 1/16" cylindrical) was impregnated for 0.1 wt. % platinum (Pt) with tetraammine platinum nitrate and calcined at 660° F. This material was then selectivated with silica by impregnating with 7.8 wt. % Dow™-550 silicone (dimethylphenylmethylpolysiloxane) in decane, stripping the decane, and calcining at 1000° F. This silica selectivation procedure was repeated three more times. The final material had an alpha value of 255.

Example 2

Steamed, 4× Silica-Selectivated, 0.1% Pt Impregnated H-ZSM-5/SiO$_2$ (Catalyst B)

Silica-bound H-ZSM-5 (0.4 μm, 26:1 Si:Al$_2$) extrudate (65/35 ZSM-5/SiO$_2$, 1/16" cylindrical) was loaded with 0.1 wt. % Pt by incipient wetness impregnation with tetraammine platinum nitrate, followed by drying at 250° F. and calcining for 1 hour in air at 660° F. The platinum-containing extrudate was then selectivated with silica by impregnating with 7.8 wt. % Dow™-550 silicone in decane, stripping the decane, and calcining. This procedure was repeated three more times. The 4× selectivated material was then steamed in 100% steam at atmospheric pressure for 24 hours at 1000° F. The final material had an alpha value of 17.

Example 3

Steamed, 3× Silica-Selectivated H-ZSM-5/SiO$_2$ (Catalyst C)

Silica-bound H-ZSM-5 (0.4 μm, 26:1 Si:Al$_2$) extrudate (65/35 ZSM-5/SiO$_2$, 1/16" cylindrical) was selectivated with silica by impregnating with 7.8 wt. % Dow™-550 silicone in decane, stripping the decane, and calcining at 1000° F. This procedure was repeated two more times. The 3× selectivated material was then steamed in 100% steam at atmospheric pressure for 24 hours at 1000° F. The final material had an alpha value of 15.

Example 4

Steamed, 0.1% Pt Impregnated, 3× Silica-Selectivated H-ZSM-5/SiO$_2$ (Catalyst D)

The catalyst of Example 3 was loaded with 0.1 wt. % Pt by incipient wetness impregnation with tetraammine platinum nitrate, followed by drying at 250° F. and calcining for 3 hours in air at 660° F. The catalyst, prior to incorporation of the hydrogenation metal, has alpha value of 15.

Example 5

Steamed, 3× Silica-Selectivated, 0.1% Pt Impregnated H-ZSM-5/SiO$_2$ (Catalyst E)

Silica-bound H-ZSM-5 (0.4 μm, 26:1 Si:Al$_2$) extrudate (65/35 ZSM-5/SiO$_2$, 1/16" cylindrical) was loaded with 0.1 wt. % Pt by incipient wetness impregnation with tetraammine platinum nitrate, followed by drying at 250° F. and calcining for 3 hours in air at 660° F. The platinum-containing extrudate was then selectivated with silica by impregnating with 7.8 wt. % Dow™-550 silicone in decane, stripping the decane, and calcining at 1000° F. This procedure was repeated two more times. The 3× selectivated material was then steamed in 100% steam at atmospheric pressure for 18 hours at 1000° F. The final material had an alpha value of 14.

Example 6

Catalytic Evaluations of Catalysts A and B

The following catalytic data were obtained using a down-flow fixed-bed reactor with the following operating conditions, unless otherwise noted: Temperature=500° C., Pressure=15 psig, H$_2$/hydrocarbon molar ratio=0.8, pure methanol and toluene feeds at 1:3 molar ratio, WHSV=3.9 h$^{-1}$ based on sieve-containing base case catalyst. The catalyst load was 2 g for the base catalyst runs. For the 1:3 molar feed mixture, the maximum toluene conversion expected from reaction with methanol would be about 33%. Methanol utilization is reported as (moles of xylene formed−moles of benzene formed)/(moles of methanol converted). Benzene is subtracted to account for any xylene formed by the disproportionation of toluene to xylene plus benzene.

Figure 2:
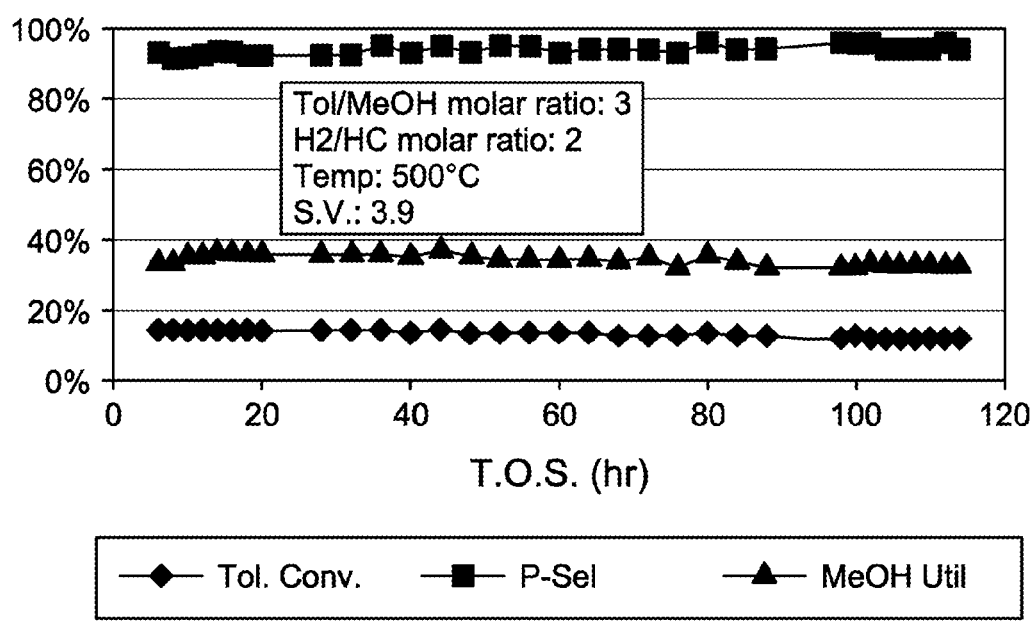

Referring now to FIG. 1, Catalyst A is impregnated with a platinum hydrogenation component, however, the test data indicates poor stability at 10 hours. Referring to FIG. 2, the data indicates that impregnation of a hydrogenation component can enhance the catalyst stability for a toluene methylation process, while maintaining high para-xylene selectivity, when the catalyst has a low alpha value.

Example 7

Catalytic Evaluations of Catalysts C, D, and E

Figure 3:
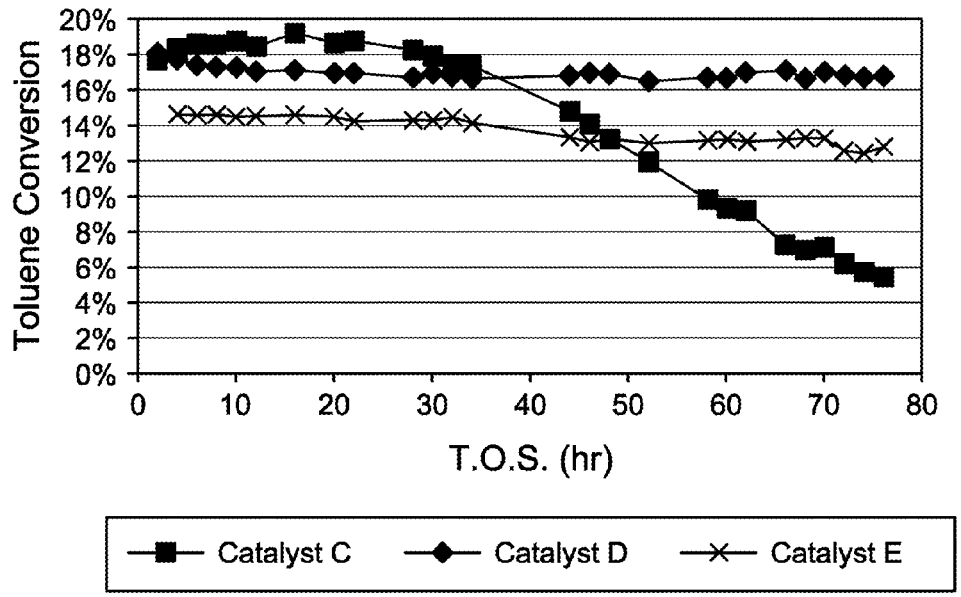
Figure 4:
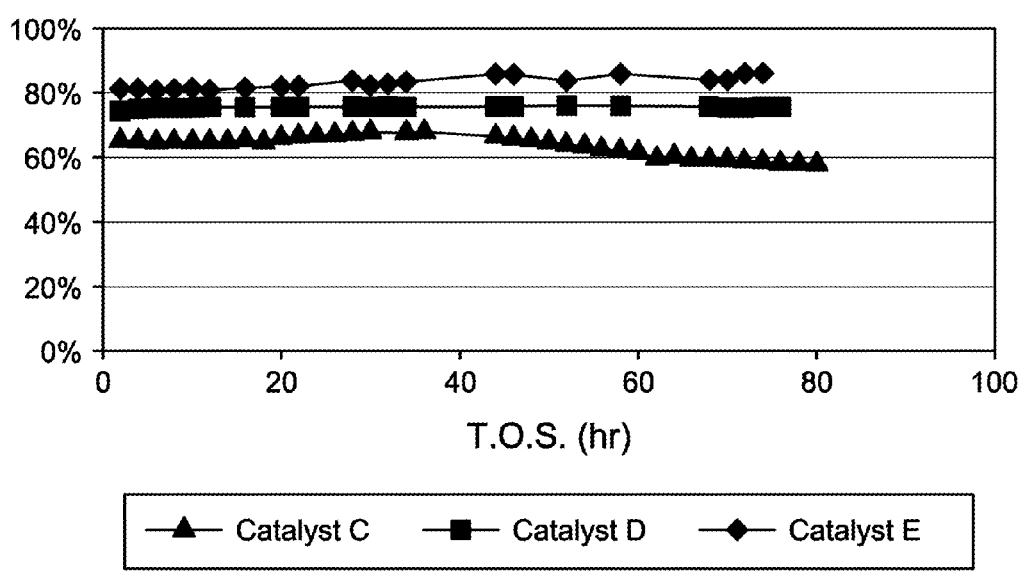
Figure 5:
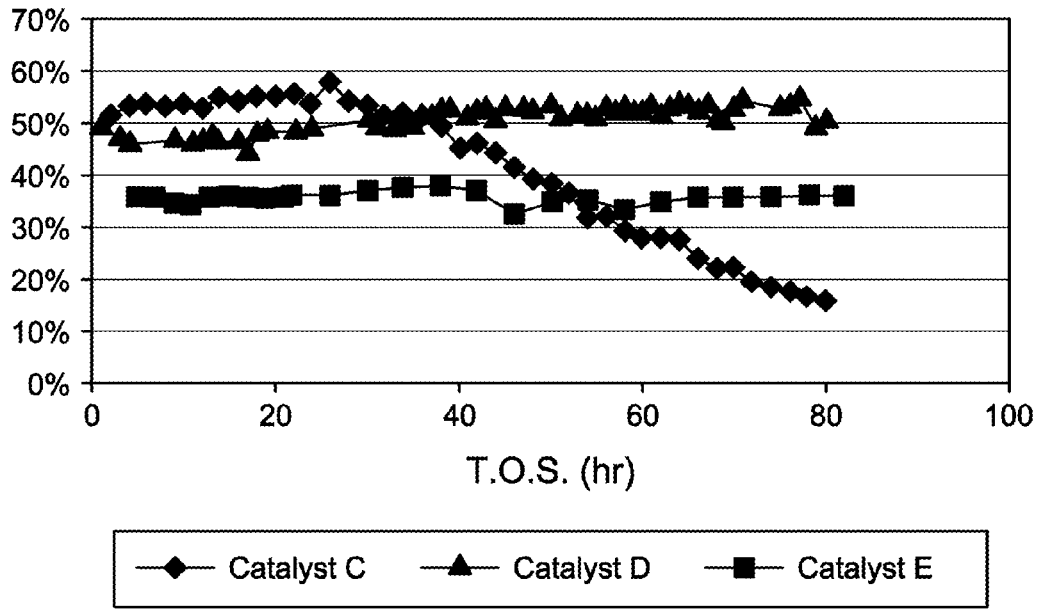

FIGS. 3-5 compare the performance of Catalysts C, D, and E. The data show that platinum incorporation into the acidic molecular sieve catalysts enhances the catalyst stability, para-xylene selectivity, and methanol utilization of the toluene methylation reaction, when the alpha value is within the criteria of this invention.

Example 8

Catalyst F

A 450:1 Si:Al$_2$ HSLS ZSM-5 molecular sieve is spray dried in a silica/alumina/clay/phosphorus matrix followed by calcination in air at 540° C. The base material is then steamed-selectivated at high temperatures (approximately 1060° C.). The resulting material had an alpha value of 2.

Example 9

0.1% Pt impregnated Catalyst F (Catalyst G)

The catalyst of Example 8 was loaded with 0.1 wt. % Pt by incipient wetness impregnation with tetraammine platinum nitrate, followed by drying at 250° F. and calcining for 3 hours in air at 660° F.

Example 10

The following catalytic data presented were obtained over Catalysts F and G using a downflow fixed-bed reactor with the following operating conditions, unless otherwise noted on the figure: Temperature=500-585° C., Pressure=40 psig, $H_2$/hydrocarbon molar ratio=2, $H_2O$/hydrocarbon molar ratio=2, pure methanol and toluene feeds at 1:2 molar ratio, WHSV=2-8 $h^{-1}$ based on sieve-containing base case catalyst. The catalyst load was 2 g. For the 1:2 molar feed mixture, the maximum toluene conversion expected from reaction with methanol would be about 50%. Methanol utilization is reported as (moles of xylene formed−moles of benzene formed)/(moles of methanol converted). Benzene is subtracted to account for any xylene formed by the disproportionation of toluene to xylene plus benzene.

Figure 6:
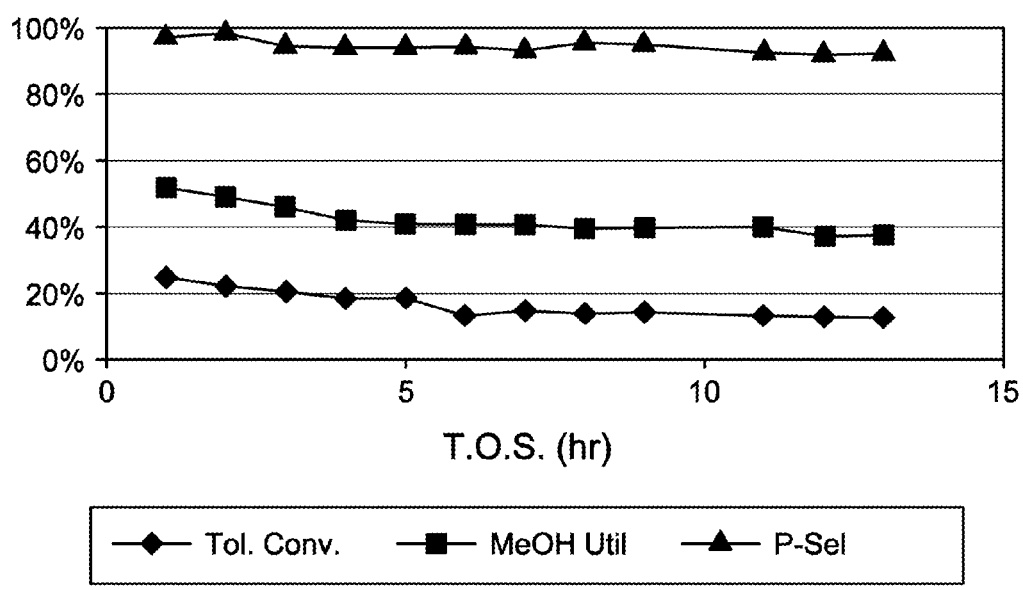

The catalytic performance for Catalyst F is shown in FIG. 6. The data show that the toluene conversion was decreased from 25% to 12% within 13 hours on stream.

Figure 7:
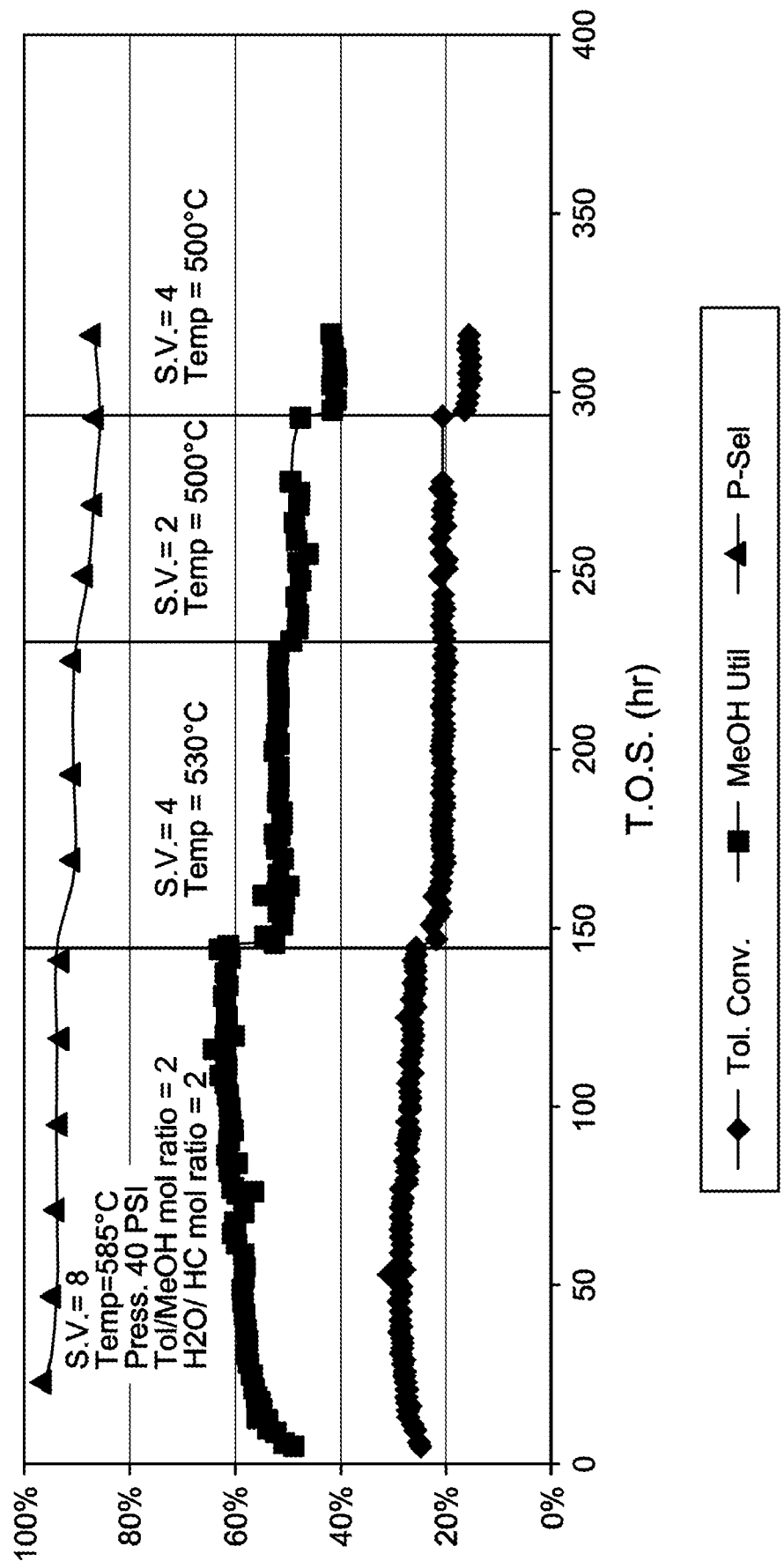

The catalytic performance of Catalyst G is shown in FIG. 7. The data show that impregnation of Catalyst F with platinum dramatically enhances the catalyst life. The catalyst activity is maintained at 150 hours.

Example 11

Catalyst H

Catalyst H is a zeolite-bound-zeolite having a core zeolite crystal comprised of ZSM-5 (70-75:1 Si:$Al_2$) bound with silica (binder content 30% of final catalyst), where the silica binder is converted to silicalite (>900:1 Si:$Al_2$). The preparation of such a zeolite-bound-zeolite is described in U.S. Pat. Nos. 5,665,325 and 5,993,642. The final material had an alpha value of 630.

Catalytic data for Examples 11-16 were obtained using a downflow fixed-bed reactor with the following operating conditions, unless otherwise noted: Temperature=500° C., Pressure=15-150 psig, $H_2$/hydrocarbon molar ratio=2, pure methanol and toluene feeds at 1:3 molar ratio, WHSV=8 $hr^{-1}$ based on sieve-containing base case catalyst. The catalyst load was 2 g for the base catalyst runs. For the 1:3 molar feed mixture, the maximum toluene conversion expected from reaction with methanol would be about 33%. Methanol utilization is reported as (moles of methanol converted)/(moles of xylene formed−moles of benzene formed). Benzene is subtracted to account for any xylene formed by the disproportionation of toluene to xylene plus benzene.

Figure 8:
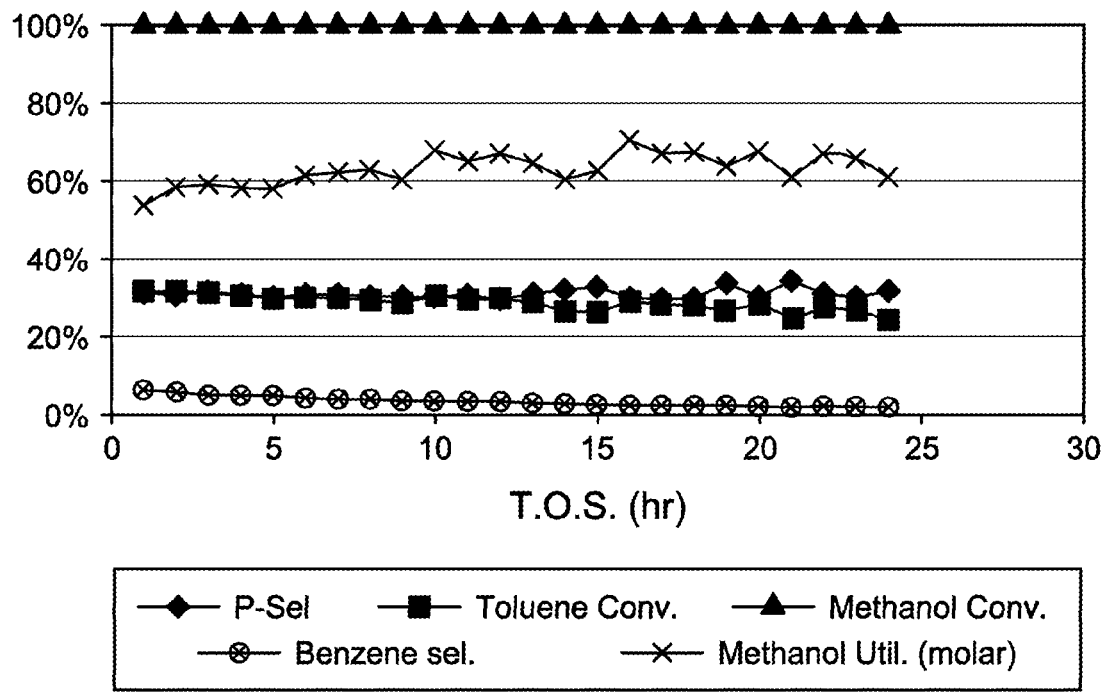

Referring to FIG. 8, the catalytic performance of the reference Catalyst H shows good stability and methanol utilization, but no enhanced para-selectivity. High initial benzene formation (7%), due to toluene disproportionation reaction, was obtained. The toluene conversion declines with the time on stream. This decline is mainly due to the loss of catalyst activity on the toluene disproportionation reaction. The benzene formation decreased from 7% to less than 2% within 24 hours.

Example 12

7 wt. % Mg Impregnated Catalyst H (Catalyst I)

Catalyst H was selectivated with 7 wt. % of magnesium (Mg) in the following manner. Ammonium nitrate hexahydrate (55.4 g) was dissolved in 27.95 g deionized water. This solution was slowly added to 100 g of Catalyst H in a rotary impregnator. The catalyst was dried at ambient conditions overnight. The catalyst was calcined at 660° F. for 3 hours in full air (3 vol/vol/min). The resulting material had an alpha value of 20.

Figure 9:
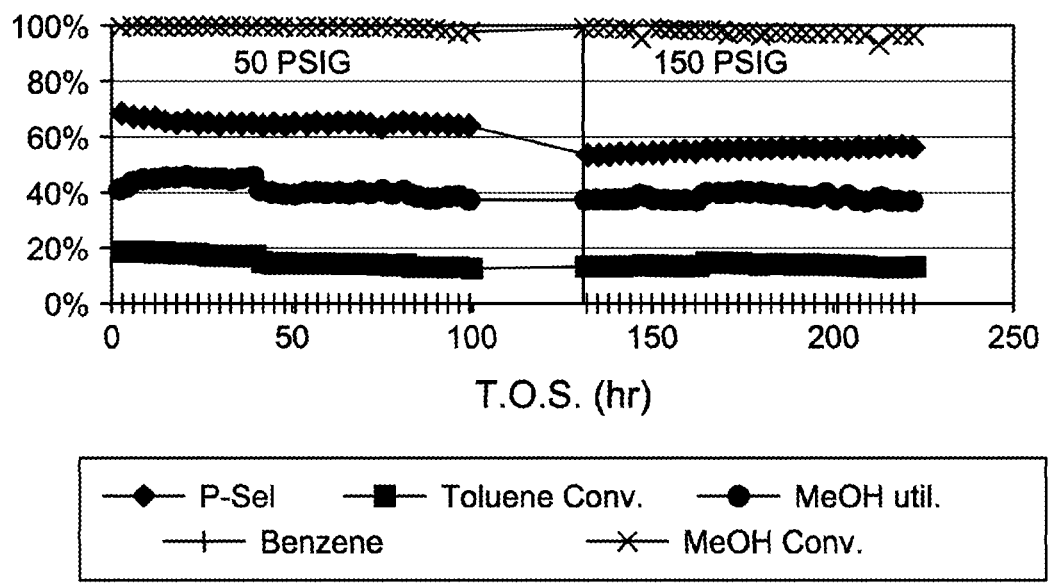

Referring now to FIG. 9, magnesium impregnation treatment boosts the para-xylene selectivity from about 30% to about 60%. However, a slight impact on the catalyst stability, toluene conversion and methanol utilization is shown. FIG. 9 also shows that higher reaction pressures (150 psig versus 50 psig) result in lower para-xylene selectivity (58% versus 65%).

Example 13

1.5 wt. % P, 7 wt. % Mg Impregnated Catalyst H (Catalyst J)

Figure 10:
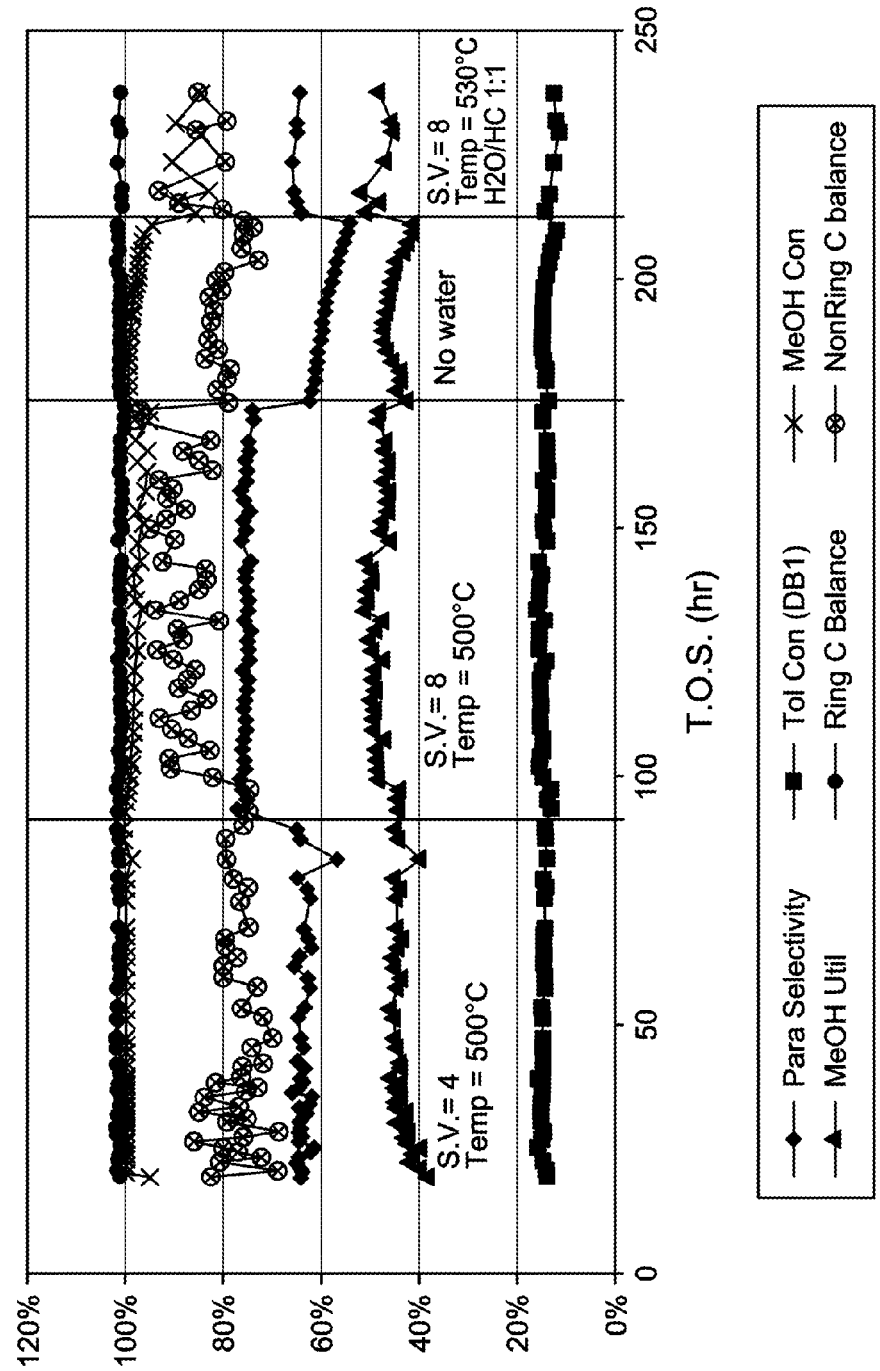

The catalyst of Example 12 was modified with 1.5 wt. % phosphorus (P), and the resulting material had an alpha value of 37. Referring to FIG. 10, Catalyst J was evaluated in a toluene methylation reaction at different hourly space velocities, with and without co-feeding water, and at different reaction temperatures. The data show that increasing the hourly space velocity from 4 to 8 resulted in higher para-xylene selectivity (78% versus 63%). In addition, the toluene conversion and methanol utilization were slightly improved.

Example 14

2.5 wt % P, 7 wt % Mg Impregnated Catalyst H (Catalyst K)

Figure 11:
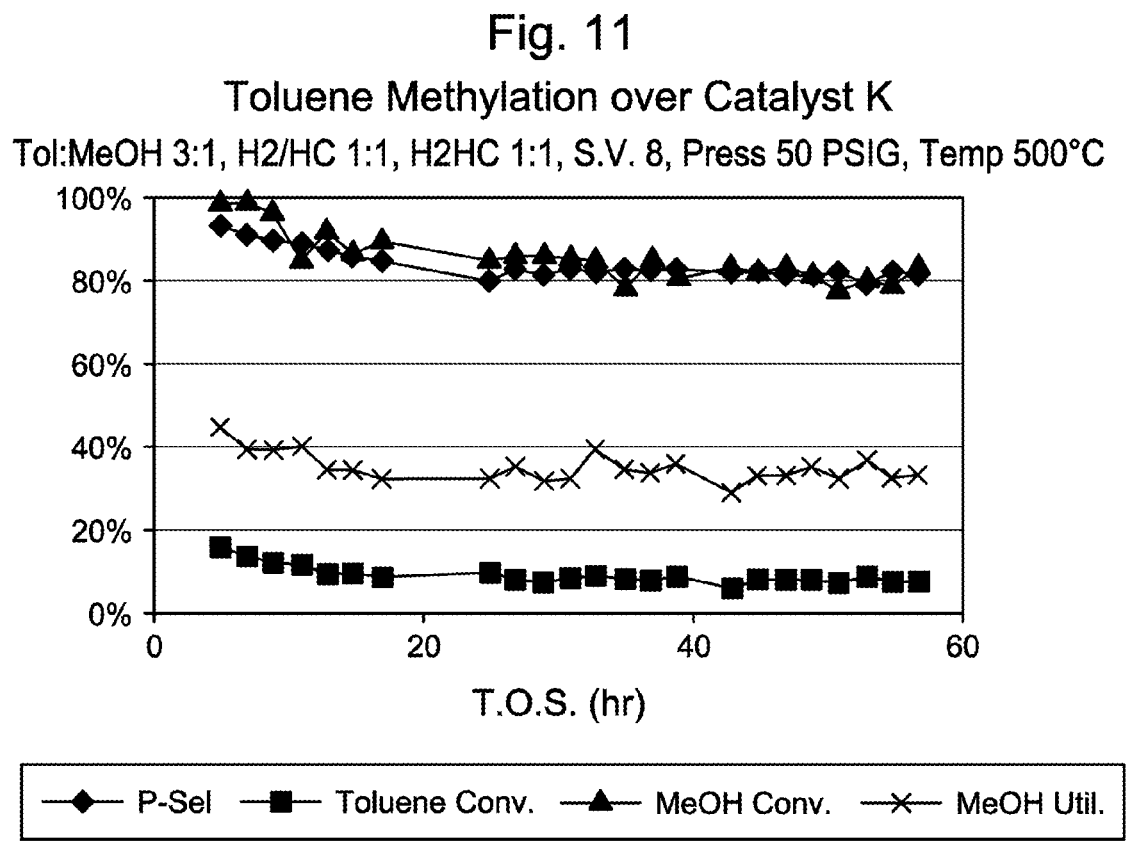

The catalyst of Example 12 was modified with 2.5 wt. % phosphorus, which resulted in a final material with an alpha value of 37. Referring now to FIG. 11, increasing the phosphorus content over the 1.5 wt. % provided in Example 13 improves the para-xylene selectivity from 75% to 93% at the same conditions. However the stability of the catalyst is affected, with the higher phosphorus content of this Example 14 deactivating the catalyst faster than the lower phosphorus content catalyst of Example 13.

Example 15

0.1 wt % Rh, 2.5 wt % P, 7 wt % Mg Impregnated Catalyst H (Catalyst L)

The catalyst of Example 14 was modified with 0.1 wt % of rhodium (Rh) as the hydrogenation component. Rhodium chloride hydrate was dissolved in deionized water. This solution was slowly added to the catalyst of Example 14 in a rotary impregnator. The catalyst was mixed well and then dried at 250° F. overnight. The catalyst was then calcined in full air at 660° F. for 3 hours (3 vol/vol/min).

Figure 12:
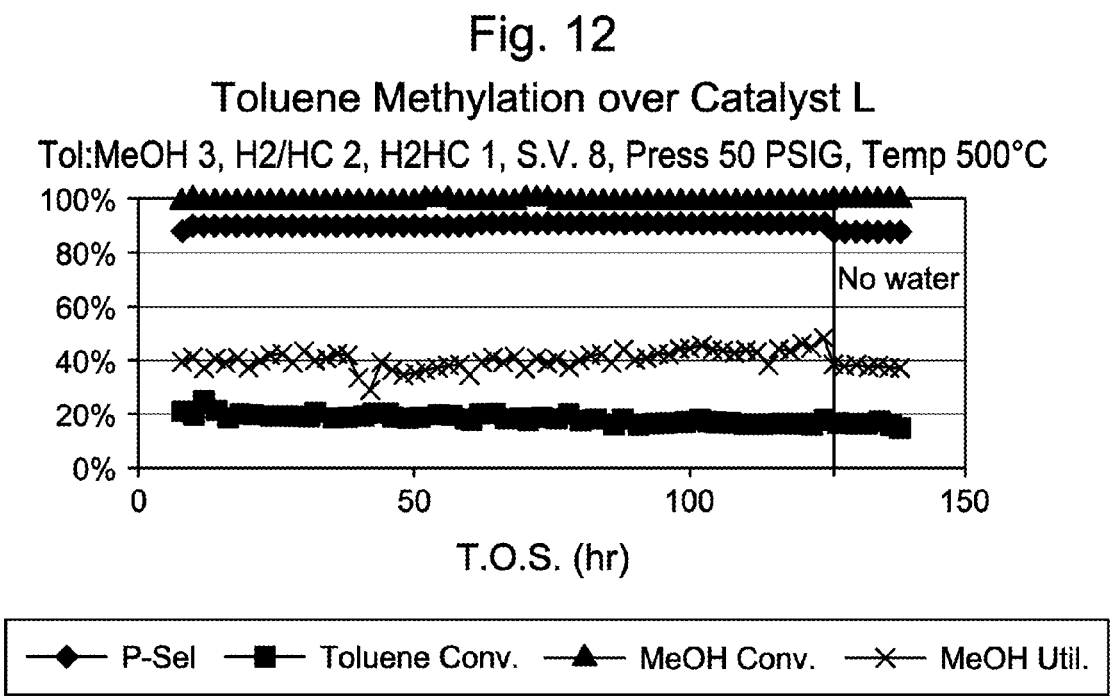

As shown in FIG. 12, significant catalyst stabilization was achieved by the addition of the hydrogenation component, rhodium, while maintaining high para-xylene selectivity.

Figure 13:
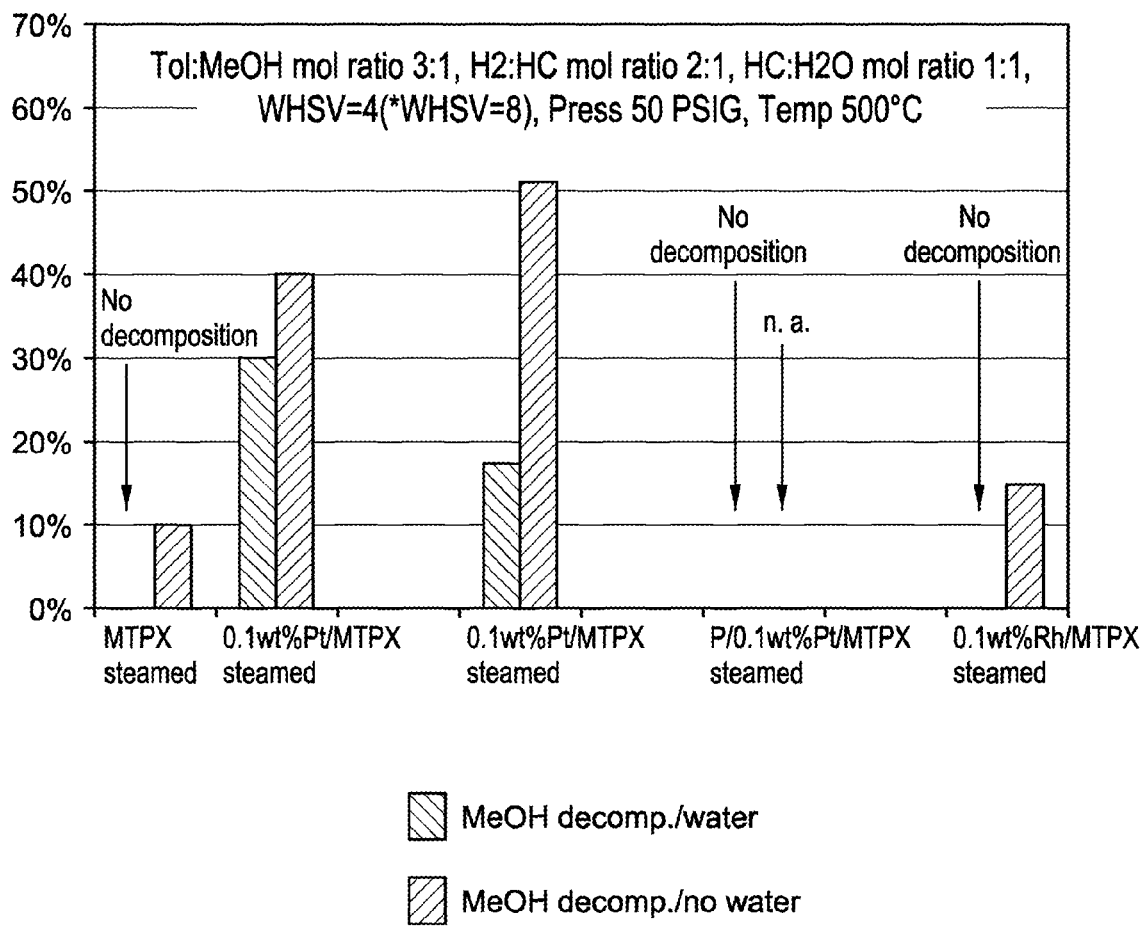
FIG. 13 is a graph showing the effect of hydrogenation metals, water and phosphorus on reducing methanol decomposition in a toluene methylation process.

Moreover, as shown in FIG. 13, gas phase analysis indicates that the use of rhodium as the hydrogenation component for a molecular sieve in accordance with this invention reduces the unwanted methanol decomposition to synthesis gas, in particular when water is co-fed into the reactor. As used in FIG. 13, the term "MTPX" refers to a 4× silica selectivated H-ZSM-5/SiO$_2$ molecular sieve. In addition, FIG. 13 shows that selectivation of the molecular sieve with phosphorus while co-feeding water inhibits the unwanted methanol decomposition to synthesis gas when used with other hydrogenation components. For example, a molecular sieve catalyst in accordance with the limitations of this invention having platinum as the hydrogenation component and phosphorus as the selectivating component has a reduced methanol decomposition to synthesis gas when water is co-feed into the reactor.

Example 16

Catalyst M

Silica-bound H-ZSM-5 (0.4 μm, 26:1 Si:Al$_2$) extrudate (65/35 ZSM-5/SiO$_2$, 1/16" cylindrical) was selectivated with silica by impregnating with 7.8 wt. % Dow™-550 silicone in decane, stripping the decane, and calcining at 1000° F. This procedure was repeated two more times. The 3× selectivated material was then steamed in 100% steam at atmospheric pressure for 12 hours at 925° F.

Magnesium nitrate hexahydrate (3.61 g) was dissolved in 13.23 g of deionized water and added to 45 g of the steamed catalyst. After mixing, the catalyst was dried overnight at 250° F. The catalyst was then calcined in full air at 1000° F. for 1 hour (5 vol/vol/min).

Ammonium phosphate (2.08 g) was dissolved in 13.46 g deionized water and slowly added to 37.22 g of the catalyst above. After mixing, the catalyst was dried at 250° F. for 2 hours. The catalyst was then calcined in full air at 660° F. for 3 hours (3 vol/vol/min).

Rhodium chloride hydrate (0.076 g) was dissolved in 9.49 g of deionized water and slowly added to 30 g of the catalyst above. The catalyst was mixed well and then dried at 250° F. for 4 hours. The catalyst was then calcined in full air at 660° F. for 3 hours (3 vol/vol/min).

The resulting catalyst had a composition of 0.1 wt. % Rh, 0.76 wt. % Mg, and 1.5 wt. % P, and an alpha value of 51, prior to incorporation of the hydrogenation component.

Figure 14:
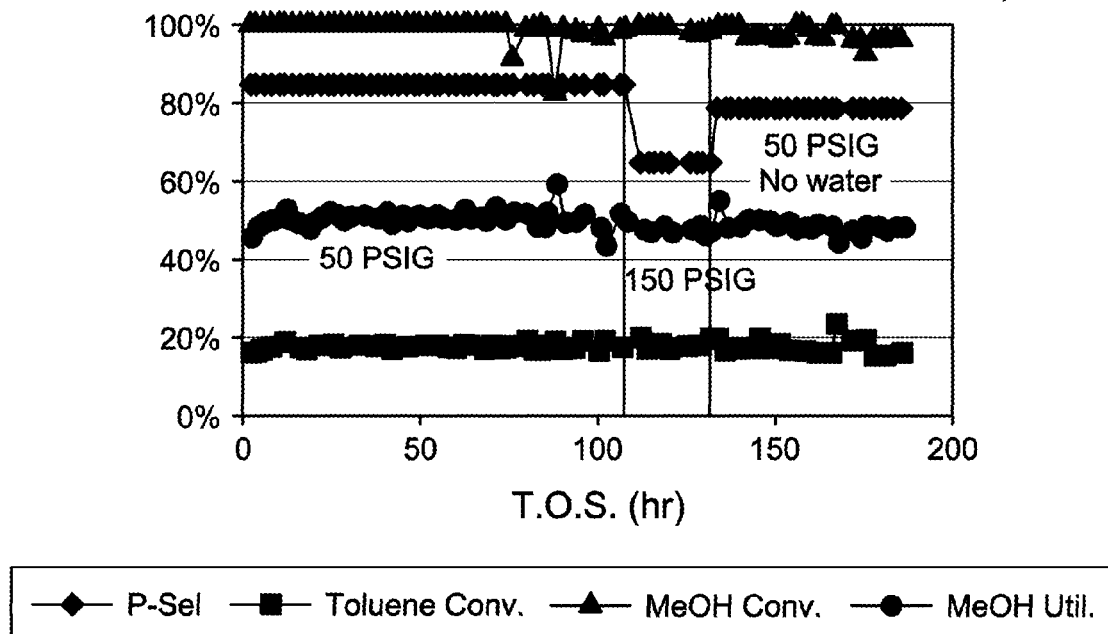

FIG. 14 shows the catalyst tested at different pressures, with and without co-feeding water. The catalyst is stable and selective.

Example 17

Steamed, 3× Silica-Selectivated H-ZSM-5/SiO$_2$

Silica-bound H-ZSM-5 (0.4 μm, 26:1 Si:Al$_2$) extrudate (65/35 ZSM-5/SiO$_2$, 1/16" cylindrical) was selectivated with silica by impregnating with 7.8 wt. % Dow™-550 silicone in decane, stripping the decane, and calcining at 1000° F. This procedure was repeated two more times. The 3× selectivated material was then steamed in 100% steam at atmospheric pressure for 24 hours at 925° F., 975° F. and 1000° F. to form three catalysts having alpha values of 51, 32 and 15, respectively.

Example 18

0.1% Pt/Al$_2$O$_3$

Alumina extrudate (100% Al$_2$O$_3$, 1/16" cylindrical) was loaded with 0.1 wt. % Pt by incipient wetness impregnation with tetraammine platinum nitrate, followed by drying at 250° F. and calcining for 3 hours in air at 660° F.

Example 19

Catalytic Evaluations

Catalytic data herein were obtained using a downflow fixed-bed reactor with the following operating conditions, unless otherwise noted: Temperature=500° C., Pressure=15 psig, H$_2$/hydrocarbon molar ratio=0.8, pure methanol and toluene feeds at 1:3 molar ratio, WHSV=3.9 h$^{-1}$ based on sieve-containing base case catalyst. The catalyst load was a mixture of 0.4-0.8 g of 0.1% Pt/Al$_2$O$_3$ of Example 18 and 2 g for the respective steamed catalyst of Example 17.

Catalyst N has a catalyst load of 0.8 g of the extrudate of Example 18 and 2 g of the steamed catalyst of Example 17 having an alpha value of 51.

Catalyst O has a catalyst load of 0.8 g the extrudate of Example 18 and 2 g of the steamed catalyst of Example 17 having an alpha value of 32.

Catalyst P has a catalyst load of 0.4 g the extrudate of Example 18 and 2 g of the steamed catalyst of Example 17 having an alpha value of 15.

For the 1:3 molar feed mixture, the maximum toluene conversion expected from reaction with methanol would be about 33%. Methanol utilization is reported as (moles of xylene formed−moles of benzene formed)/(moles of methanol converted). Benzene is subtracted to account for any xylene formed by the disproportionation of toluene to xylene plus benzene.

Figure 15:
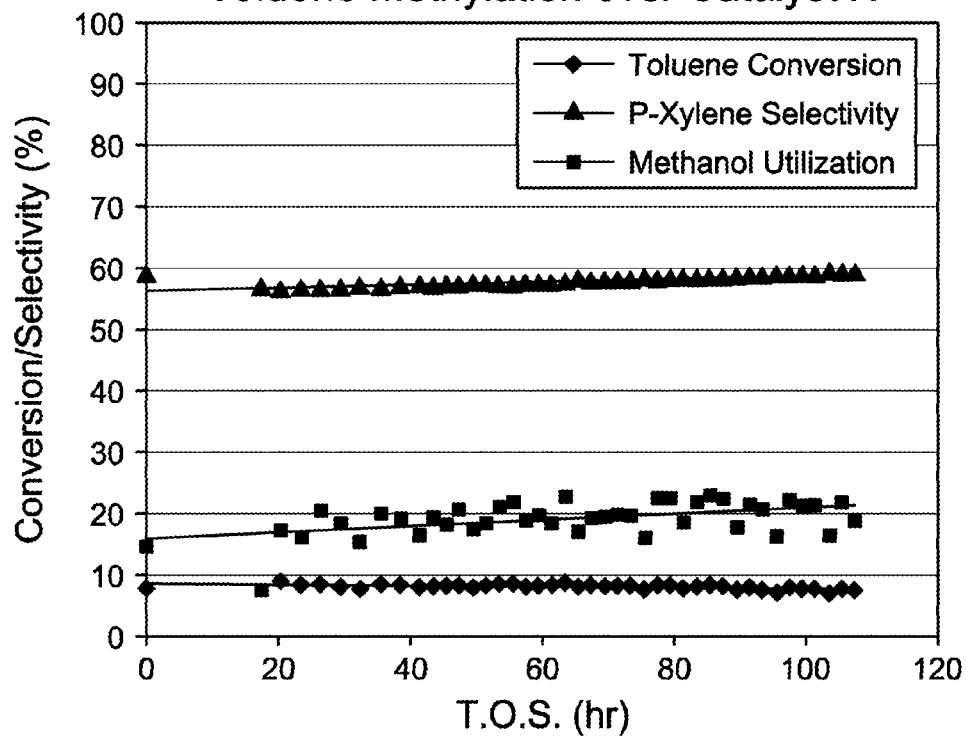
Figure 16:
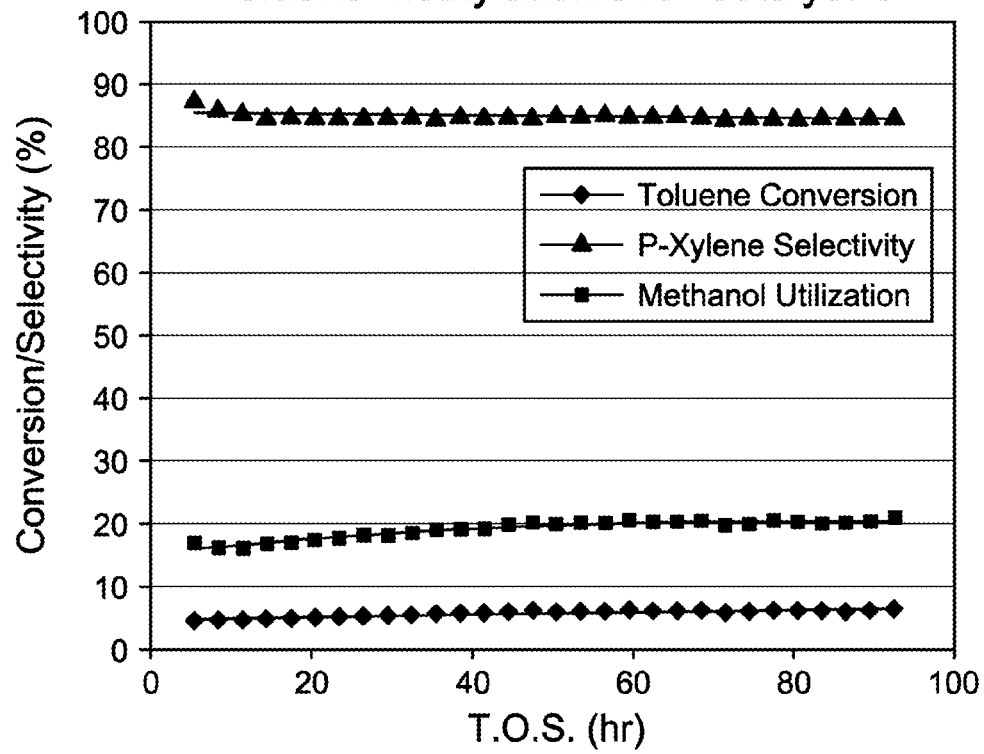
Figure 17:
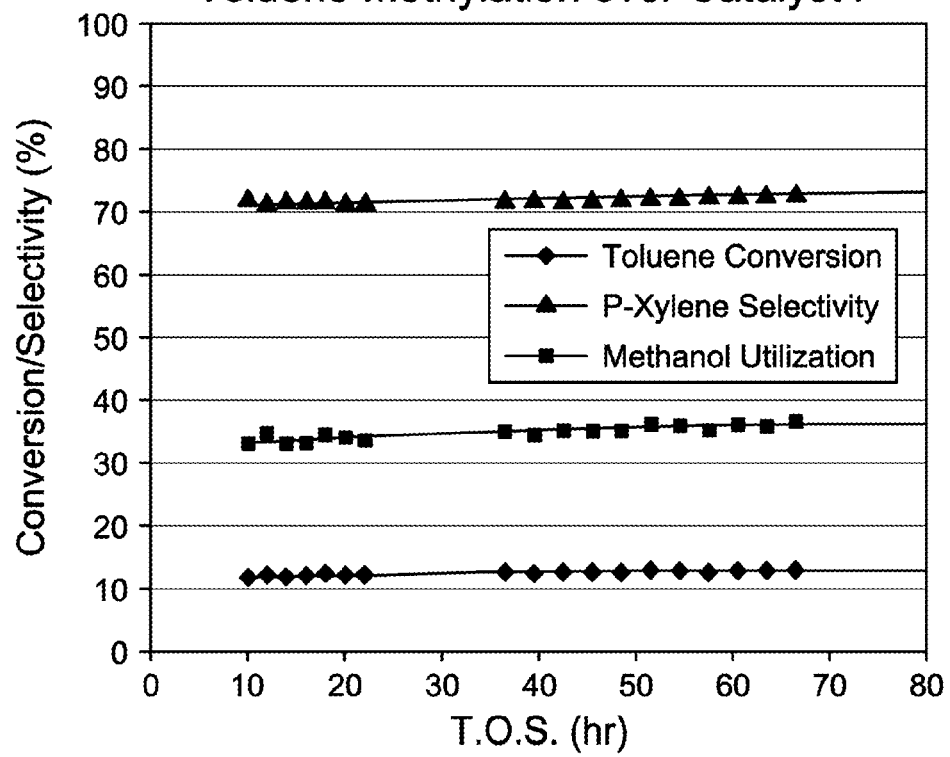

As shown in FIGS. 15-17, each of Catalyst N, O and P indicate good stability. Catalyst O appears to maintain the highest para-xylene selectivity of 85% with toluene conversion at 7%. Catalyst P exhibits the highest toluene conversion at 14% with good para-xylene selectivity of 73%. This Example indicates that the hydrogenation function does not have to be located directly on the molecular sieve to be effective in accordance with this invention, as long as the hydrogenation function is in proximity to the molecular sieve. As shown in this example, the hydrogenation metal can be impregnated onto an amorphous support that is co-mingled with the active molecular sieve catalyst.

Example 20

0.1% Rh, 3× Silica-Selectivated, 1% P Impregnated ZSM-5/SiO$_2$(Catalyst Q)

Silica bound H-ZSM-5 (450:1 Si:Al$_2$) extrudate (50/50 ZSM-5/SiO$_2$, 1/16" cylindrical) was loaded with 1 wt. % P by incipient wetness impregnation with ammonium phosphate, drying at 250° F. and calcining for 3 hours in air at 1000° F. The phosphorus containing extrudate was then selectivated with silica by impregnating with 7.8 wt. % DOW™-550 silicone in decane, stripping the decane, and calcining at 1000° F. This procedure was repeated two more times. The 3× selectivated material was then loaded with 0.1 wt. % Rh by incipient wetness impregnation with rhodium chloride hydrate, drying at 250° F., and calcining for 3 hours in air at 660° F. The resulting catalyst had a composition of 0.1 wt. %

Rh and 1 wt. % P and an alpha value of 1, prior to incorporation of the hydrogenation component.

Figure 18:
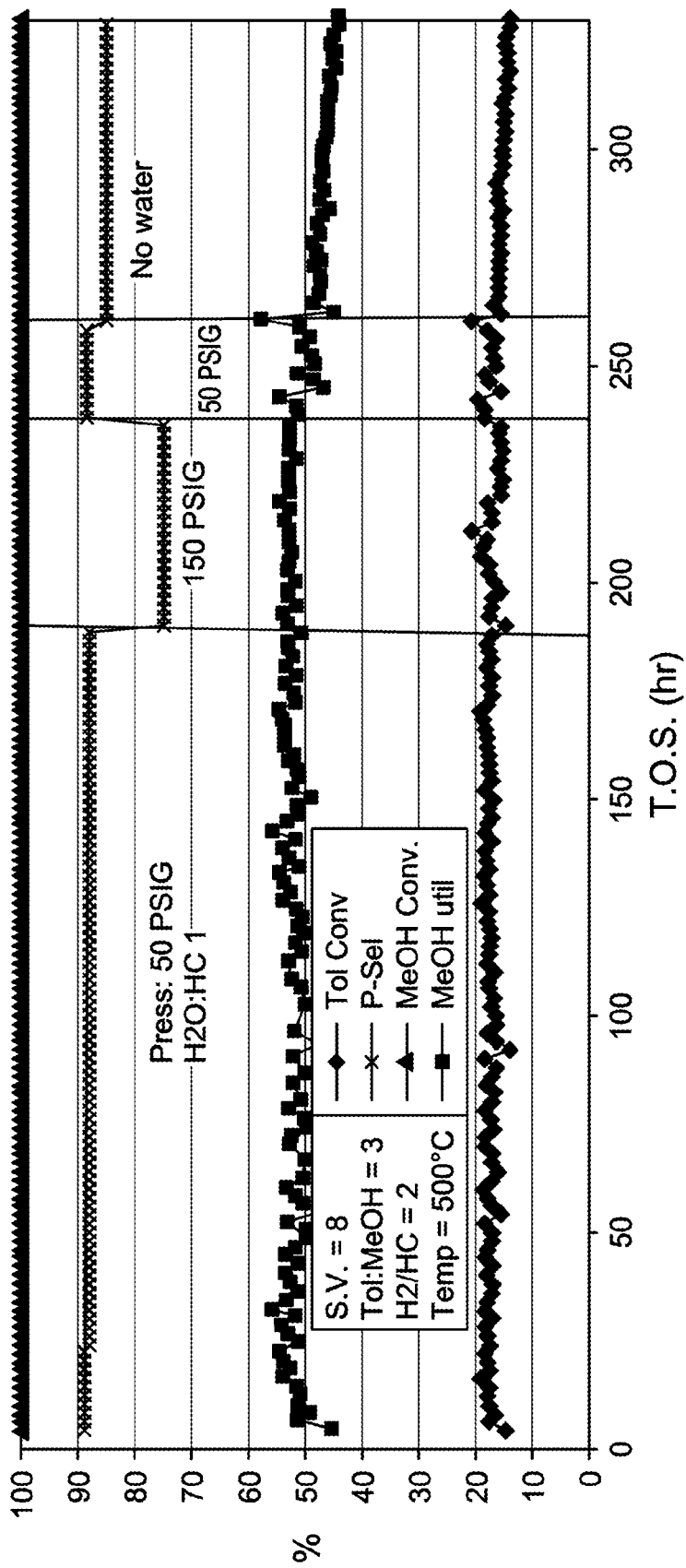

Referring now to FIG. 18, catalytic data shows that Catalyst Q maintains high para-selectivity and excellent catalyst stability.

What is claimed is:

1. A process for forming xylene comprising reacting an alkylating agent comprising methanol with a feed comprising toluene in the presence of a catalyst under alkylation reaction conditions to produce a product containing xylene, said catalyst comprising a selectivated ZSM-5 molecular sieve and at least one hydrogenation metal selected from Pt and Rh, wherein at least one of the following conditions is satisfied:
   a. said selectivated molecular sieve has an alpha value of less than 100 prior to incorporation of said at least one hydrogenation metal, or
   b. said selectivated and hydrogenated molecular sieve has an alpha value of less than 100.

2. The process recited in claim 1, wherein said molecular sieve is selectivated by treatment with a phosphorus compound and a silicon compound.

3. The process recited in claim 2, wherein said silicon compound comprises silicones and silicone polymers.

4. The process recited in claim 3, wherein said treatment with said silicones and silicone polymers comprises multiple treatments with said silicones and silicone polymers.

5. The process recited in claim 1, wherein said molecular sieve is selectivated by treatment with a phosphorus compound, a magnesium compound and a silicon compound.

6. The process recited in claim 5, wherein said silicon compound comprises silicones and silicone polymers.

7. The process recited in claim 6, wherein said treatment with said silicones and silicone polymers comprises multiple treatments with said silicones and silicone polymers.

8. The process recited in claim 1, wherein said molecular sieve comprises a zeolite-bound-zeolite molecular sieve.

9. The process recited in claim 8, wherein said zeolite-bound-zeolite comprises a ZSM-5 core zeolite crystal bound with silica, wherein said silica binder is converted to silicalite.

10. The process recited in claim 9, wherein said ZSM-5 core zeolite crystal has a silica to alumina ratio of from about 70:1 to 75:1 $Si:Al_2$.

11. The process recited in claim 9, wherein said binder comprises from about 25 wt. % to about 45 wt. % based upon the weight of said zeolite-bound-zeolite.

12. The process recited in claim 9, wherein said zeolite-bound-zeolite has a silica to alumina ratio of greater than 900:1 $Si:Al_2$.

13. The process recited in claim 8, wherein said molecular sieve is selectivated by treatment with a phosphorus compound and a magnesium compound.

14. The process of claim 1, wherein said selectivated molecular sieve has an alpha value of less than 100 prior to incorporation of said at least one hydrogenation metal.

15. The process of claim 1, wherein said selectivated and hydrogenated molecular sieve has an alpha value of less than 100.

16. The process of claim 1, wherein said molecular sieve is a silicon compound selectivated molecular sieve.

* * * * *